(12) United States Patent
Dev et al.

(10) Patent No.: US 6,865,416 B2
(45) Date of Patent: Mar. 8, 2005

(54) ELECTRICALLY INDUCED VESSEL VASODILATION

(75) Inventors: Nagendu B. Dev, San Diego, CA (US); Sukhendu B. Dev, San Diego, CA (US); Gunter A. Hofmann, San Diego, CA (US)

(73) Assignee: Genetronics, Inc., San Diego, CA (US)

( * ) Notice: Subject to any disclaimer, the term of this patent is extended or adjusted under 35 U.S.C. 154(b) by 0 days.

(21) Appl. No.: 09/969,367

(22) Filed: Oct. 1, 2001

(65) Prior Publication Data

US 2002/0016615 A1 Feb. 7, 2002

Related U.S. Application Data

(63) Continuation of application No. 09/307,216, filed on May 7, 1999, now Pat. No. 6,347,247.
(60) Provisional application No. 60/084,857, filed on May 8, 1998.

(51) Int. Cl.[7] .................................................. A61N 1/36
(52) U.S. Cl. ......................................................... 607/2
(58) Field of Search ...................... 607/1, 2, 39, 50–52, 607/137, 138, 143

(56) References Cited

U.S. PATENT DOCUMENTS

| | | | |
|---|---|---|---|
| 5,135,478 A | * | 8/1992 | Sibalis .......................... 604/20 |
| 5,304,120 A | | 4/1994 | Crandell et al. |
| 5,498,238 A | | 3/1996 | Shapland et al. |
| 5,501,662 A | | 3/1996 | Hofmann |
| 5,507,724 A | | 4/1996 | Hofmann et al. |
| 5,554,119 A | | 9/1996 | Harrison et al. |
| 5,626,576 A | * | 5/1997 | Janssen ........................ 606/41 |
| 5,634,899 A | | 6/1997 | Shapland et al. |
| 5,690,691 A | * | 11/1997 | Chen et al. ................... 607/133 |
| 5,704,908 A | * | 1/1998 | Hofmann et al. .............. 604/21 |
| 5,944,710 A | | 8/1999 | Dev et al. |
| 6,014,584 A | | 1/2000 | Hofmann et al. |
| 6,026,326 A | * | 2/2000 | Bardy .......................... 607/133 |
| 6,132,419 A | | 10/2000 | Hofmann |
| 6,149,681 A | | 11/2000 | Houser et al. |
| 6,219,577 B1 | | 4/2001 | Brown, III et al. |

* cited by examiner

*Primary Examiner*—George R. Evanisko
(74) *Attorney, Agent, or Firm*—Daniel M. Chambers; Douglas C. Murdock; BioTechnology Law Group

(57) ABSTRACT

The invention provides methods for inducing or increasing the vasodilation of a vessel. The invention further provides methods for inducing or increasing the flow of fluid through a vessel. An electrical impulse is applied to the vessel in order to induce or increase vessel vasodilation or to induce or increase the flow of fluid through the vessel. In a particular embodiment, a novel double-balloon catheter system incorporating electroporation technology has been designed and is used to apply the electrical impulse endoluminally.

12 Claims, 8 Drawing Sheets

Porous Balloon Electroporation Catheter

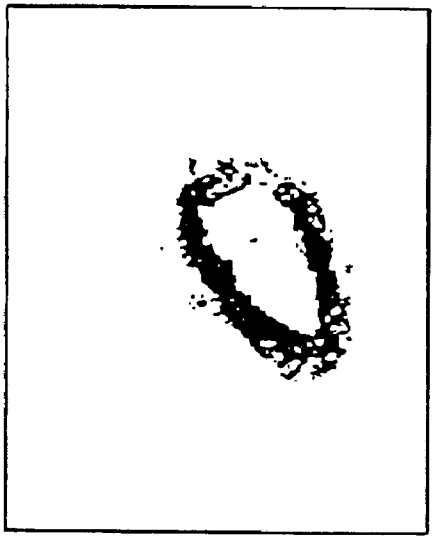
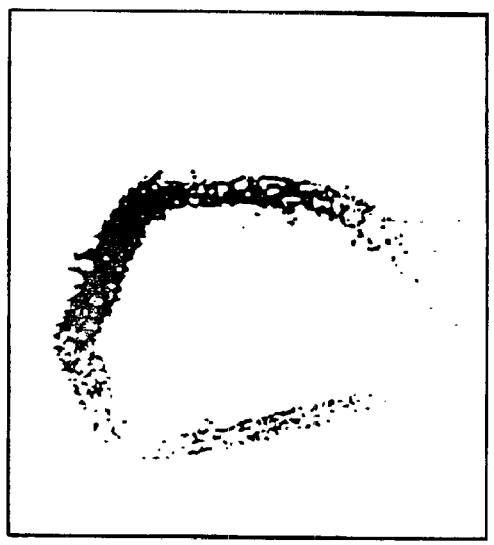
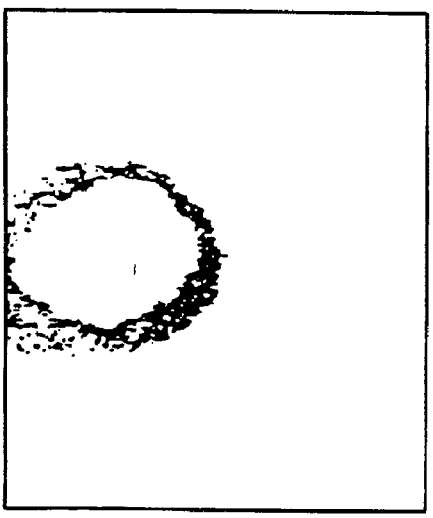
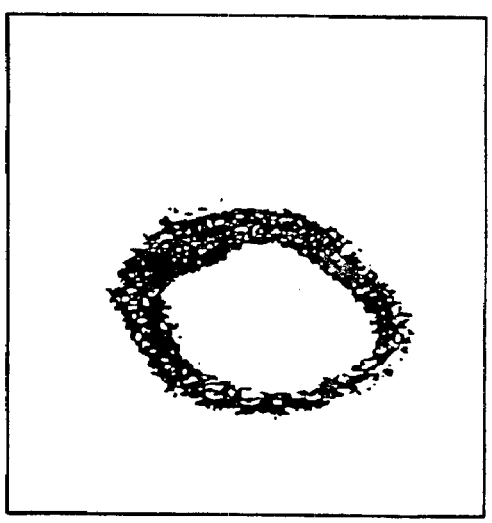
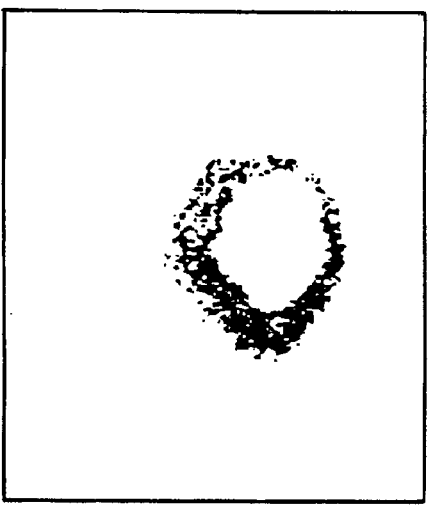
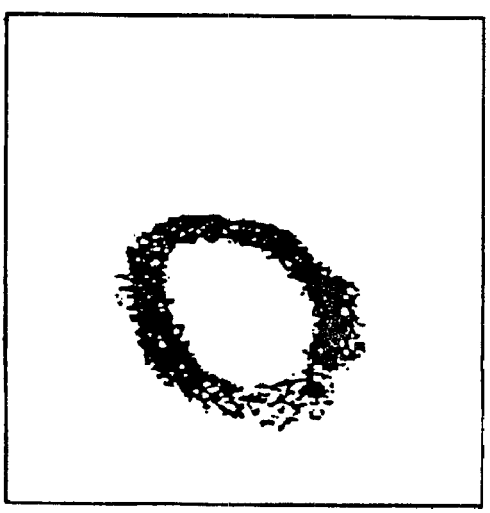
FIG. 5A
FIG. 5B

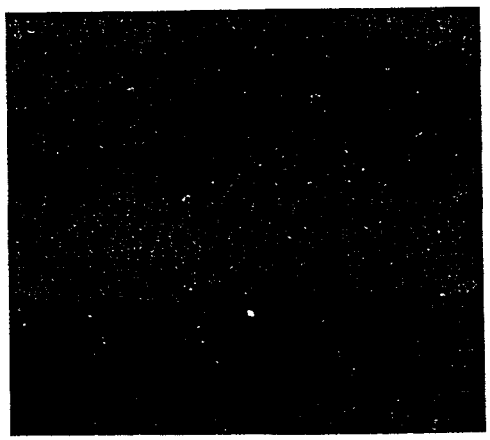
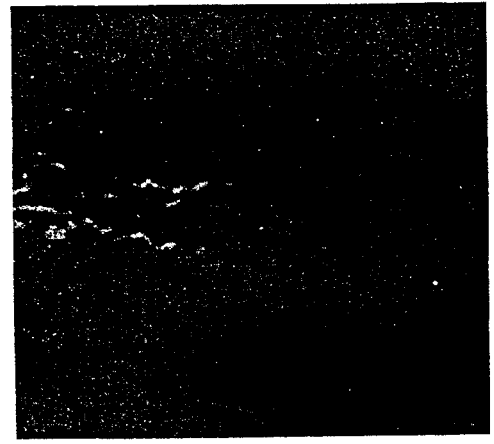
FIG. 7A
FIG. 7B

ELECTRICALLY INDUCED VESSEL VASODILATION

RELATED APPLICATIONS

Under 37 U.S.C. §119(e)(1), this application claims the benefit of prior U.S. provisional application 60/084,857, filed May 8, 1998 and U.S. application Ser. No. 09/307,216, filed May 7, 1999 now U.S. Pat. No. 6,347,247.

FIELD OF THE INVENTION

The present invention relates to the field of vessel vasodilation and, more particularly, to methods for inducing or increasing the vasodilation of a vessel and methods for inducing or increasing the flow of fluid through a vessel by applying an electrical impulse to the vessel.

BACKGROUND OF THE INVENTION

Despite procedural success rates greater than 95% achieved by percutaneous transluminal coronary angioplasty (PTCA), luminal renarrowing of blood vessels after balloon angioplasty occurs in 30% to 60% of all cases within 3 to 6 months. Smooth muscle cell proliferation and extracellular matrix remodeling appear to play pivotal roles in the luminal renarrowing process and negate the beneficial effect of vascular reconstruction by angioplasty (Leclercq et al., *Arch. Mal. Coeur. Vaiss*. 89:359–365 (1996)). The use of new technology, such as atherectomy, excimer laser, stent or rotablator (Hofling et al., *Z. Kardiol*. 80:25–34 (1991); Margolis et al., *Clin. Cardiol*. 14:489–493 (1991); Serruys et al., *J. Am Coll. Cardiol*. 17:143B–154B (1991); Warth et al., *J. Am. Coll. Cardiol*. 34:641–648 (1994)) has not been able to reduce the incidence of restenosis significantly.

A variety of drugs also have been investigated to prevent luminal renarrowing in experimental animal and clinical settings, but without much success. A primary reason for this may be the failure of systemic administration to achieve effective concentrations of drugs at the targeted area. To overcome this deficiency, new endoluminal catheter delivery systems with various balloon configurations have been employed for localizing drug delivery. These include: hydrogel balloon, laser-perforated (Wolinsky balloon), 'weeping,' channel and 'Dispatch' balloons and variations thereof (Azrin et al., *Circulation* 90:433 (1994); Consigny et al., *J. Vasc. Interv. Radiol* 5:553 (1994); Wolinsky et al., *JACC*, 17:174B (1991); Riessen et al., *JACC* 23:1234 (1994); Schwartz, Restenosis Summit VII, Cleveland, Ohio, 1995, pp 290–294). Delivery capacity with hydrogel balloon is limited and, during placement, the catheter can lose substantial amount of the drug or agent that is administered. High pressure jet effect in Wolinsky balloon can cause vessel injury which can be avoided by making many holes, <1 $\mu$m, (weeping type). The 'Dispatch' catheter has generated a great deal of interest for drug delivery as it creates circular channels and can be used as a perfusion device, allowing continuous blood flow. However, each of these devices have limitations and have not been successful in resolving the problem of restenosis.

The cell membrane may be transiently permeabilized by subjecting cells to a brief, high intensity, electric field. This pulse-induced permeabilization of cell membranes, termed electroporation, has been used by investigators to introduce various compositions such as DNA, RNA, proteins, liposomes, latex beads, whole virus particles and other macromolecules into living cells (Hapala, *Crit. Rev. Biotechnol*. 17:105–122 (1997)). In particular, for example, large size nucleotide sequences (up to 630 Kb) can be introduced into mammalian cells via electroporation (Eanault et al., *Gene* 144:205 (1994); *Nucl. Acids Res*. 15:1311 (1987); Knutson et al., *Anal. Biochem*. 164:44 (1987); Gibson et al., *EMBO J*. 6:2457 (1987); Dower et al., *Genetic Engineering* 12:275 (1990); Mozo et al., *Plant Molecular Biology* 16:917 (1991)). These studies show that electroporation affords an efficient means to deliver therapeutic compositions such as drugs, genes, polypeptides and the like in vivo by applying an electrical pulse to particular cells or tissues within a subject.

Several therapeutic applications of electroporation are now being explored: treatment of restenosis using angioplasty combined with electroporation to deliver drugs to a localized portion of coronary or peripheral arteries (Shapland et al., U.S. Pat. No. 5,498,238); treatment of cancer by electroporation in the presence of low doses of chemotherapeutic drugs (Mir, U.S. Pat. No. 5,468,223); introduction of functional genes for gene therapy (Nishi et al., *Cancer Research* 56:1050–1055 (1996)), electroporation of skin for the delivery of drugs into the skin or for the transdermal delivery of drugs across tissue (Zhang et al., *Biochem. Biophys. Res. Comm*. 220:633–636 (1996)); Weaver et al., U.S. Pat. No. 5,019,034; Prausnitz, *Adv. Drug. Deliv*. 18:395–425 (1996)). Hofmann describes a syringe apparatus for electroporating molecules and macromolecules into tissue regions in vivo in which the needles of the syringe used to deliver the molecules also function as electrodes (U.S. Pat. No. 5,273,525). Weaver describes an apparatus for the delivery of chemical agents into tissues in vivo via electroporation (U.S. Pat. No. 5,389,069). Hofmann et al., describe methods for delivering genes or drugs via electroporation to treat endothelial and other cells of blood vessels, for example, and an electroporation catheter device that can be used to practice the methods (U.S. Pat. No. 5,507,724). Crandell et al. describe the use of a catheter apparatus for introducing therapeutic macromolecules via electroporation into endothelial cells of a patients' blood vessels (U.S. Pat. No. 5,304,120).

However, in view of the limited success in preventing luminal renarrowing after angioplasty, a need exists for the development of methods for inducing or increasing vessel vasodilation in order to treat undesirable vessel narrowing without therapeutic compositions, many of which elicit adverse side effects. The present invention satisfies this need and provides related advantages as well.

SUMMARY OF THE INVENTION

In accordance with the present invention, there are provided methods for inducing or increasing vasodilation of a vessel in a subject by applying an electrical impulse to the vessel, having sufficient strength and duration to induce or increase vasodilation of the vessel. Methods for inducing or increasing the flow of fluid through a vessel in a subject by applying an electrical impulse to the vessel, having sufficient strength and duration to induce or increase the flow of fluid through the vessel, also are provided. For example, a method of the invention employs an electrical impulse applied via electroporation. A method of the invention applies an electrical impulse with an electro-catheter apparatus. Invention methods are useful for treating clinical situations in which it is desired to increase or induce vessel vasodilation or to induce or increase the flow of fluid through the vessel.

Multiple electrical impulses can be applied in a method of the invention. An electrical impulse can be applied from about 50 to 90 volts per 1.5 mm. An electrical impulse can be applied for about 0.5 ms to 10 ms. Vessels can be denuded prior to, simultaneously with or after applying an electrical impulse in a method of the invention in order to augment the induction of vessel vasodilation or increase in the flow of fluid through the vessel.

Compositions can be administered to the vessel in the subject prior to, simultaneously with or after the application of an electrical impulse. Compositions can be administered locally or systemically. For example, a composition that inhibits cell proliferation, such as that associated with intimal thickening or hyperplasia or that inhibits platelet adhesion or aggregation, PDGF action, or matrix synthesis can be administered. Compositions useful in a method of the invention include but are not limited to are heparin, low molecular weight heparin and hirudin as well as angiotensin-converting enzyme inhibitor, colchicine, somatostatin analog and serotonin antagonist. Drugs, polynucleotides, polypeptides and chemotherapeutic agents also are included. A method of the invention can deliver a composition into the tunica intima, tunica media or tunica adventitia of the vessel, for example.

In another embodiment, the invention includes a method for inducing or increasing vasodilation of a vessel in a subject by applying an electrical impulse to the vessel using a catheter apparatus having at least one inflatable balloon portion, a first electrode, a second electrode positioned with respect to the first electrode and the subject where an electric field sufficient to induce or increase vasodilation of the vessel is generated by the electrical impulse. For example, a catheter apparatus having at least one infusion passage for administering a composition into a vessel of the subject is useful in a method of the invention. In one aspect, electrodes are positioned within the vessel.

BRIEF DESCRIPTION OF THE DRAWINGS

FIGS. 5A and 5B show a sample of a tissue section from either non-pulsed arteries (A) or pulsed arteries (B). Electroporation of the artery was performed using four exponential pulses of 66 volts at 9.6 msec over a period of 15 seconds. Tissue images were taken five hours after applying the pulses. Images were taken at equal magnification in which the guidewire for inserting the catheter serves as the return electrode.

FIGS. 7A and 7B show pseudocolor images of the pulsed (A) and non-pulsed (B) artery. Fluorescence intensity increases from red (lowest in the color value ladder) to blue, green, yellow, fire-red and finally to white. The approximate values that correspond to the indicated colors are as follows: red=2; deep blue=82; green=176; yellow=215 and white>255. Both pulsed arteries and non-pulsed arteries received 20 units/Kg F-heparin locally through a double-balloon catheter in which the guidewire for inserting the catheter serves as the return electrode.

DETAILED DESCRIPTION OF THE INVENTION

Figure 1:
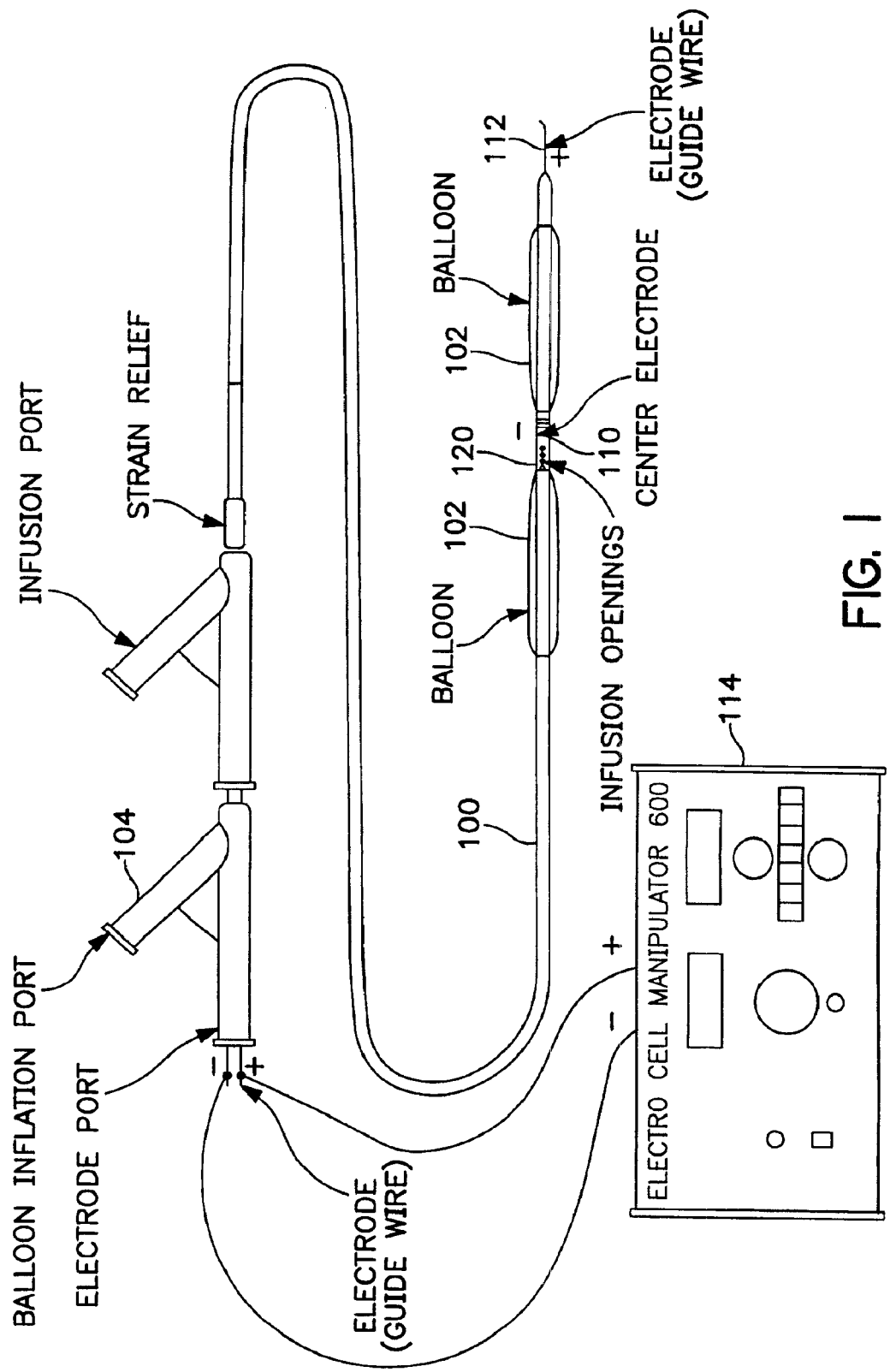
FIG. 1 is a schematic diagram of an exemplary endoluminal double-balloon electroporation catheter (EPC) in which the guidewire for inserting the catheter serves as the return electrode, and an ECM 600 exponential pulse generator.

The present invention is based on the seminal discovery that application of an electrical impulse to a vessel can induce the vasodilation of that vessel. A method of the invention utilizes an electrical impulse which, when applied to a vessel at a sufficient strength and duration, induces the vasodilation of the vessel. The invention therefore provides methods for inducing or increasing vessel vasodilation in a subject and methods for inducing or increasing the flow of fluid through a vessel in a subject.

The methods of the invention are advantageous in several respects. For example, the methods allow for the induction of vessel vasodilation or allow for increasing the flow of fluid through a vessel without the presence of exogenous therapeutic compositions having potentially toxic side effects. Thus, the methods of the invention are particularly applicable in treating clinical situations of vessel narrowing or blockage where the systemic use of drugs is undesirable, for example, due to toxicity. The methods of the invention are additionally advantageous when a composition is administered to the vessel. For example, drugs that can function to induce or increase vessel vasodilation or that can function to induce or increase the flow of fluid through a vessel, when administered to the vessel to which an electrical impulse is to be applied, can function additively or synergistically with the electrical impulse to produce a greater induction or increase of vessel vasodilation or greater induction or increase in the flow of fluid through a vessel than that produced by electropulsing alone.

As used herein, the terms "impulse," "pulse," "electrical impulse," "electrical pulse," "electropulse" and grammatical variations thereof are interchangeable and all refer to an electrical stimulus. Although the various terms are frequently used herein in the singular, the singular forms of the terms can refer to multiple pulses. Preferred electrical impulses are those applied via electroporation.

As used herein, the term "vessel" means any tube within the body of a subject or a hollow channel through an organ of a subject to which an electrical impulse can be applied. Vessels include, for example, blood vessels, such as arteries, veins and capillaries, and gastrointestinal vessels such as the esophagus, larynx, small intestine and large intestine (i.e., colon). Vessels also include lymphatic vessels, ducts etc. The methods of the invention are applicable to any vessel of any size in a subject. Preferred vessels contain smooth muscle cells (e.g., myocytes). Examples of preferred vessels are the carotid artery, coronary artery, femoral artery iliac artery and aorta.

As used herein, the term "lumen" refers to the interior portion of a vessel. The lumen can be an area substantially devoid of the material which comprises a vessel, or a "cavity" within a vessel, in which case the term "luminal cavity" is used, or can refer to an inner cellular layer of vessel (e.g., vessel endothelium, extracellular matrix etc.) which surrounds a "cavity," in which case the term "luminal vessel layer" or "luminal lining" is used. Thus, in a blood vessel, a "luminal cavity" would refer to the portion of the vessel through which blood can flow and a "luminal vessel layer" would refer to an inner layer or lining of the vessel that surrounds the luminal cavity.

The term "vasodilation" or "dilation" or grammatical variations thereof, when used as a modifier of the term "vessel," means that the vessel has expanded in comparison to a non-electrically pulsed vessel. Vessel expansion generally occurs in the luminal cavity or in the luminal vessel layer and is indicated by an increase in the area or diameter of the luminal cavity, an increase in the area or circumference of the luminal vessel layer or, by an increase in the circumference or outer diameter of the vessel. Although not wishing to be bound by any particular theory, the induction or increase of vessel vasodilation by an electrical impulse appears to result either from a direct effect caused by the electrical current applied to the vessel, or an indirect effect resulting from the release or stimulation of factors that promote vasodilation, such as the release of endothelium derived relaxation factors (EDRF) currently identified as nitric oxide (NO) or other vasodilating substances triggered by the electrical pulses applied to the cells of the vessel.

As used herein, the term "fluid" refers to a mobile composition that passes or transits through a vessel. A fluid therefore includes, for example, blood, lymphatic fluid, urine, or enzyme containing liquids such as bile as well as any material which passes through the gastrointestinal tract, such as food or liquid that passes through the esophagus, and the digested material that passes through the various stages of the gastrointestinal tract (i.e., small intestine and colon). The phrase "flow of fluid" refers to the velocity or volume of a fluid that passes through a vessel. Thus, the phrase "inducing the flow of fluid" means that the fluid now proceeds through the vessel in which, prior to applying an electrical impulse, essentially no fluid flow occurred (e.g., a blocked vessel). The phrase "increasing the flow of fluid" means that the amount of fluid that passes through the vessel is greater than that which occurs in the vessel, for example, prior to applying an electrical impulse (e.g., a partially obstructed or narrowed vessel).

As used herein, the term "subject" refers to any animal that has a vessel. It is envisioned that the methods for inducing or increasing vasodilation of a vessel and the methods for inducing or increasing the flow of fluid through a vessel described herein can be performed on any animal. Preferably, the subject is a human.

The invention provides a method for inducing or increasing the vasodilation of a vessel in a subject by applying an electrical impulse to the vessel at a sufficient strength and duration to induce or increase vasodilation of the vessel. The invention further provides a method for inducing or increasing the flow of fluid through a vessel in a subject by applying an electrical impulse to the vessel at a sufficient strength and duration to induce or increase the flow of fluid through the vessel.

Figure 6:
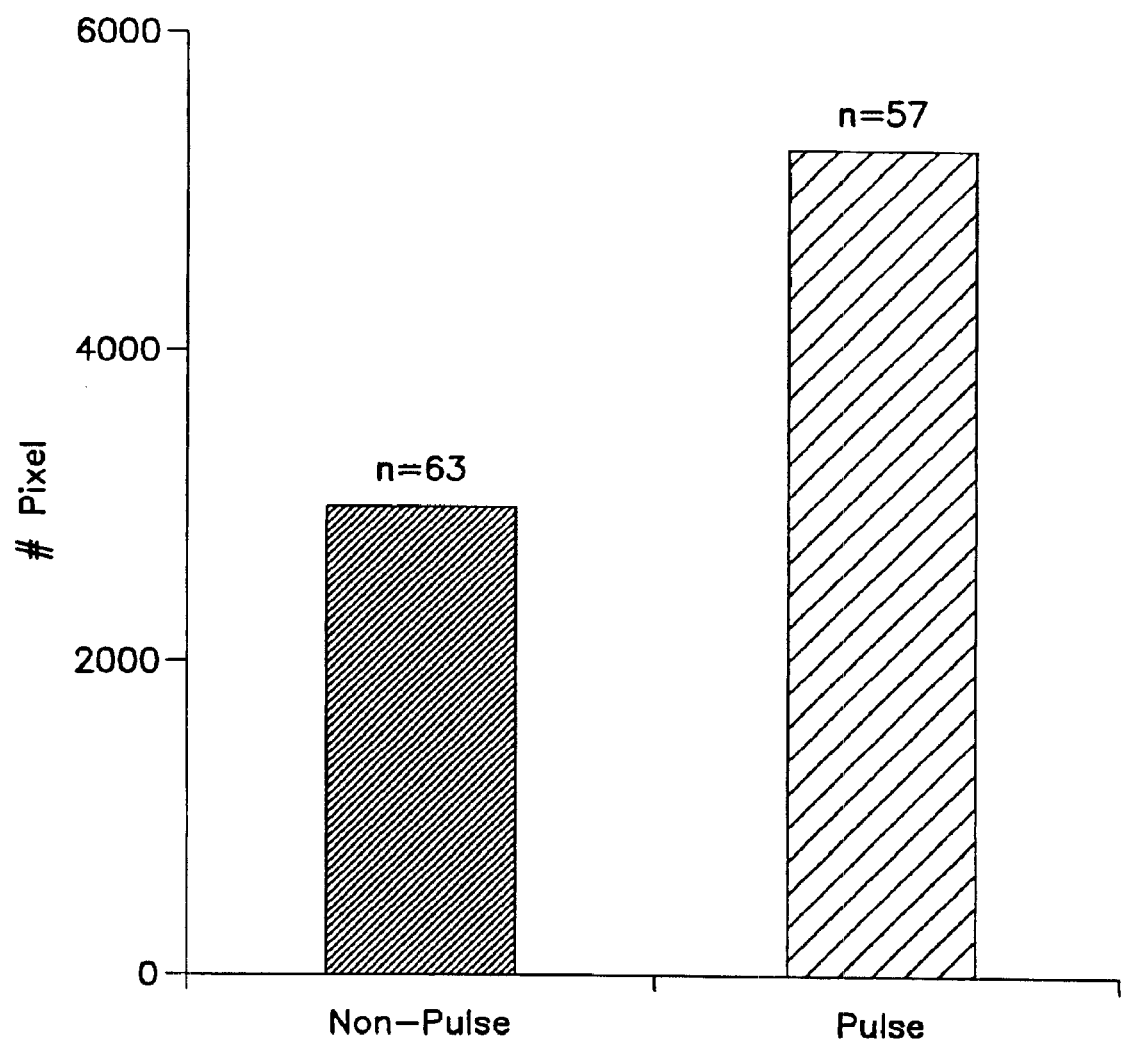
FIG. 6 is a bar graph showing the effect of electrical pulsing on the luminal area of the artery. The value plotted as the total number of pixels (Y-axis) is a relative measure of the area inside the lumen of the vessel. The data was obtained from eight different experiments; "n" is the number of arterial sections for each sample in which the guidewire for inserting the catheter serves as the return electrode.

Any electrical impulse capable of inducing or increasing vessel vasodilation or inducing or increasing the flow of fluid through a vessel can be used to practice the methods of the invention. Exemplary means with which to apply an electrical impulse to a vessel is via electroporation. Exemplary electropulsing parameters for inducing the vasodilation of an artery via electroporation were as follows: one pulse having a pulse width of about 9.0 msec at approximately 63 volts applied to the vessel endoluminally (Example II). The effect of an electrical impulse applied via electroporation to the lumen layer of an artery, as observed histologically, is shown in FIG. 5. The results showing an increase in the area of the luminal cavity of the artery after electropulsing are shown in FIG. 6.

Thus, in one embodiment, the methods of the invention are practiced by applying an electrical impulse to a vessel via electroporation.

The electropulsing parameters exemplified for arteries are applicable to blood vessels in general as blood vessels have similar cell structure, electrical resistance, matrix structure etc. Additionally, other vessels which have a comparable smooth muscle cell content and electrical resistance, etc., to blood vessels also can be electropulsed using electropulsing parameters similar to those exemplified for blood vessels. For example, although the gastrointestinal tract (e.g., small, large intestine) is functionally distinct from blood vessels, it is contemplated that the electropulsing parameters will be comparable to blood vessels due, in part, to the similar smooth muscle cell content and electrical resistance.

Differences between vessel cell type, the presence or absence of extracellular matrix, wall thickness, the presence of a stenotic lesion (soft plaque vs. hard), and electrical resistance are likely to require manipulation of the electropulsing parameters for inducing or increasing vessel vasodilation or for inducing or increasing the flow of fluid for particular vessels. The electropulsing parameters that may be manipulated include, for example, applying the pulse to the vessel exo- or endo-luminally, the position of the electrodes relative to the vessel (closer or further), the type and number of electrodes, the length and diameter of the vessel region pulsed and the administration of a composition prior to, substantially contemporaneously with or after electropulsing. For example, for an electrically resistive vessel (e.g., one containing a hard stenosis) pulse duration or the number of pulses can be increased. Ultrafast CT scan can be used to determine the presence or extent of stenotic calcification. By placing the electrode in direct contact with the vessel, reduced pulse length can be used to induce a similar degree of vessel vasodilation.

Electropulsing parameters may include denuding a vessel before, during or after an electrical impulse is applied. As used herein, the term "denude" or "denuding" refers to the removal of all, a substantial portion, or any part of the cells that comprise a vessel. Denuding the endothelial lining of a vessel prior to applying an electrical impulse may "potentiate" or "augment" the induction of vessel vasodilation or an increase in the flow of fluid through the vessel. As used herein, the term "potentiate" or "augment" means any action (e.g., mechanical, physical) or composition that can enhance, stimulate, or promote the induction of vessel vasodilation or the increase in flow of fluid through a vessel produced by an electropulse. "Potentiating" compositions include compositions that either induce vessel vasodilation or the flow of fluid through a vessel independent of an electrical impulse (e.g., heparin) or compositions whose function is associated with an electrical impulse (i.e., generally do not function to induce vessel vasodilation or to increase flow of fluid through a vessel independent of an electrical pulse).

Electropulsing parameters also include electrical parameters. Appropriate electrical parameters may vary and will depend on the vessel chosen, whether or not the vessel is blocked and, if blocked, to what extent. For example, for a rabbit blood vessel, about six pulses having a voltage ranging from about 50 to 90 volts with a duration of about 10 to 15 msec is applied to the vessel when one of the electrodes is positioned between two balloons of an endoluminally inserted catheter is preferred. Electrical parameters that can be manipulated therefore include pulse strength, pulse wave form, duration, the number of pulses applied and the time between pulses, for example. The particular electropulsing and electrical parameters for inducing or increasing vessel vasodilation or for inducing or increasing the flow of fluid through any vessel can be determined using the teachings herein and the general knowledge of those having skill in the art.

Suitable electric pulses for practicing the invention methods include, for example, square wave pulses, exponential waves, unipolar oscillating wave forms, bipolar oscillating wave forms, other wave forms generating electric fields, or a combination of any of these forms. Each pulse wave form has particular advantages. For example, square wave form pulses are advantageous due to increased cell transformation efficiencies in comparison to exponential decay wave form pulses, and the ease of optimization over a broad range of voltages (Saunders, "Guide to Electroporation and Electrofusion," 1991, pp. 227–47). Preferably, the waveform used for a method of the invention is an exponential or a square wave pulse. In the methods of the invention where compositions are administered in order to deliver the composition into a vessel, square wave electrical pulses are preferred.

It is desired that the electric field produced by a pulse be as homogeneous as possible and of the correct amplitude so as to prevent excessive cell lysing. Generally, the strength of the electric field will range from about 50 volts/cm to about several KV/cm. The field strength is calculated by dividing the voltage by the distance (calculated for 1 cm separation; expressed in cm) between the electrodes. Thus, if the voltage is 500 volts between two electrode faces which are 0.5 cm apart, then the field strength is 500/(0.5) or 1000 volts/cm or 1 KV/cm. Preferably, the amount of voltage applied between the electrodes is in the range of about 10 volts to 200 volts, and more preferably from about 50 to 90 volts.

The pulse length can be from about 100 microseconds ($\mu$s) to 100 milliseconds (ms), preferably from about 500 $\mu$s to 100 ms and more preferably from about 1 ms to 10 ms. There can be from about 1 to 100 pulses applied to a vessel. Preferably, the number of pulses is from about 1 to 50 pulses and more preferably from about 1 to 10 pulses. The time between pulses can be one second or longer. The electric field strength, waveform type, pulse duration and number of pulses depend upon the construction of the device used to apply the electrical pulse and can be adjusted as appropriate according to the particular vessel to which the electric pulse is applied, and whether compositions are to be administered before or substantially contemporaneously with the electrical pulse.

The various electrical parameters, including electric field strengths, are similar to the electric fields needed for in vivo cell electroporation, which are similar in amplitude to the electric fields required for in vitro cell electroporation. Each cell has its own critical field strength for optimum electroporation due to cell size, membrane make-up and individual characteristics of the cell membrane itself. For example, the field strength required generally varies inversely with the size of the cell. Mammalian cells typically require about 0.5 to 5.0 KV/cm before cell death or electroporation occur. A database containing the various electrical parameters for in vivo and in vitro cell electroporation is maintained by Genetronics, Inc. (San Diego, Calif.). The electrical parameters used for in vitro and in vivo electroporation of various cell types also are known in the art and can be found in research papers and in various electroporation protocols provided by commercial vendors (e.g., Bio-Rad Catalogue, 1996, pp. 293–302, and the references cited at page 302).

Therefore, appropriate electrical parameters for inducing the vasodilation of a vessel or for increasing the flow of fluid through a vessel can be based upon the electrical parameters used for the in vitro electroporation of the predominant cell type that comprises the vessel. Alternatively, electrical parameters can be empirically determined by applying an impulse and detecting an induction or increase of vessel vasodilation or an induction or increase in the flow of fluid through the vessel. For example, an electrical impulse can be applied to a vessel and induction of vessel vasodilation or an increase in the flow of fluid through a vessel can be detected using the histological methods exemplified herein or other methods known in the art. If the induction of vessel vasodilation or increase in the flow of fluid through the vessel is less than desired, the strength or duration of the pulse can be increased from the initial setting, or multiple pulses can be applied. Multiple electrical impulses also can be applied in order to regulate the rate at which vessel vasodilation is induced (rapid vs. slow) or to increase the degree to which a vessel is vasodilated. Similarly, multiple electrical impulses can be applied in order to increase the rate at which the flow of fluid through a vessel is increased.

As the induction or increase of vessel vasodilation is detected by an expansion of the luminal cavity, the luminal vessel layer or of the outer diameter of a vessel, a variety of methods can be employed in order to detect vessel vasodilation. In particular, for example, the histological methods set forth in Example II can be used to detect expansion of the luminal vessel layer and the vessel cavity of an artery in response to the electrical impulse. Specific (e.g., tissue, cell, etc.) or non-specific marker stains or labeling agents, which can visualize smaller vessels or increase the detail of the visualized vessel can be used alone or in combination with these histological methods. If the vessel is physically large enough or the induction of vessel vasodilation is great enough, visual inspection of the vessel can detect induction or an increase of vessel vasodilation. Other methods useful for the detection of vessel vasodilation are known in the art including, for example, intravascular ultrasound (IVUS) and vascular angioscopy which measures luminal cross sectional area of a vessel (Nissen et al., Circulation 88:1087–99 (1993); Mallery et al., Am. Heart J. 119:1392–1400 (1990); McPherson, Sci. American March/April, pp. 22–31 (1996); and Baptista et al., Eur. Heart J. 16:1603–12 (1995), which are incorporated herein by reference).

An induction or increase in the flow of fluid through a vessel can similarly be detected using the exemplified histological methods as well as the above-described methods known in the art for detecting vessel vasodilation. Additionally, other assays known in the art can be useful for detecting an induction or increase in the flow of fluid through a vessel. For example, illumination of a vessel by barium can be used to detect the induction or an increase in the flow of fluid through the gastrointestinal tract.

In another embodiment, an electrical impulse is applied to a vessel with a catheter apparatus. In one aspect, an electroporation catheter (EPC) or similar apparatus inserted endoluminally into a vessel is used to apply an electrical impulse. In this aspect, the electrodes are positioned within the vessel near the region where the electrical impulse is to be applied. After one or more pulses are applied, the EPC is withdrawn from the vessel.

An endoluminal electroporation catheter useful in practicing the methods invention of the invention needs to satisfy several requirements: A pulsed field with a field strength of about 100 volts/cm needs to be created at the vessel wall; the pulse length is typically in the order of milliseconds. The pulsed field should generally be confined to the area of the vessel to be dilated, with the main vector of the electric field pointing into the vessel wall. Other design aspects concern the electrode geometry and the electric field for a given potential difference (voltage) between electrodes; it is desirable to maximize the electric field for a given potential difference (electrical efficiency) (Hofmann, Cells in electric fields: physical and practical electronic aspects of Electro cell fusion and electroporation. In Neumann E, Sowers A and Jordan C (eds): "Electroporation and Electrofusion in Cell Biology," New York: Plenum Press, 1989, pp 389–407). Electrostatic field plots of catheter configurations can be useful in determining this electrical efficiency.

Figure 2:
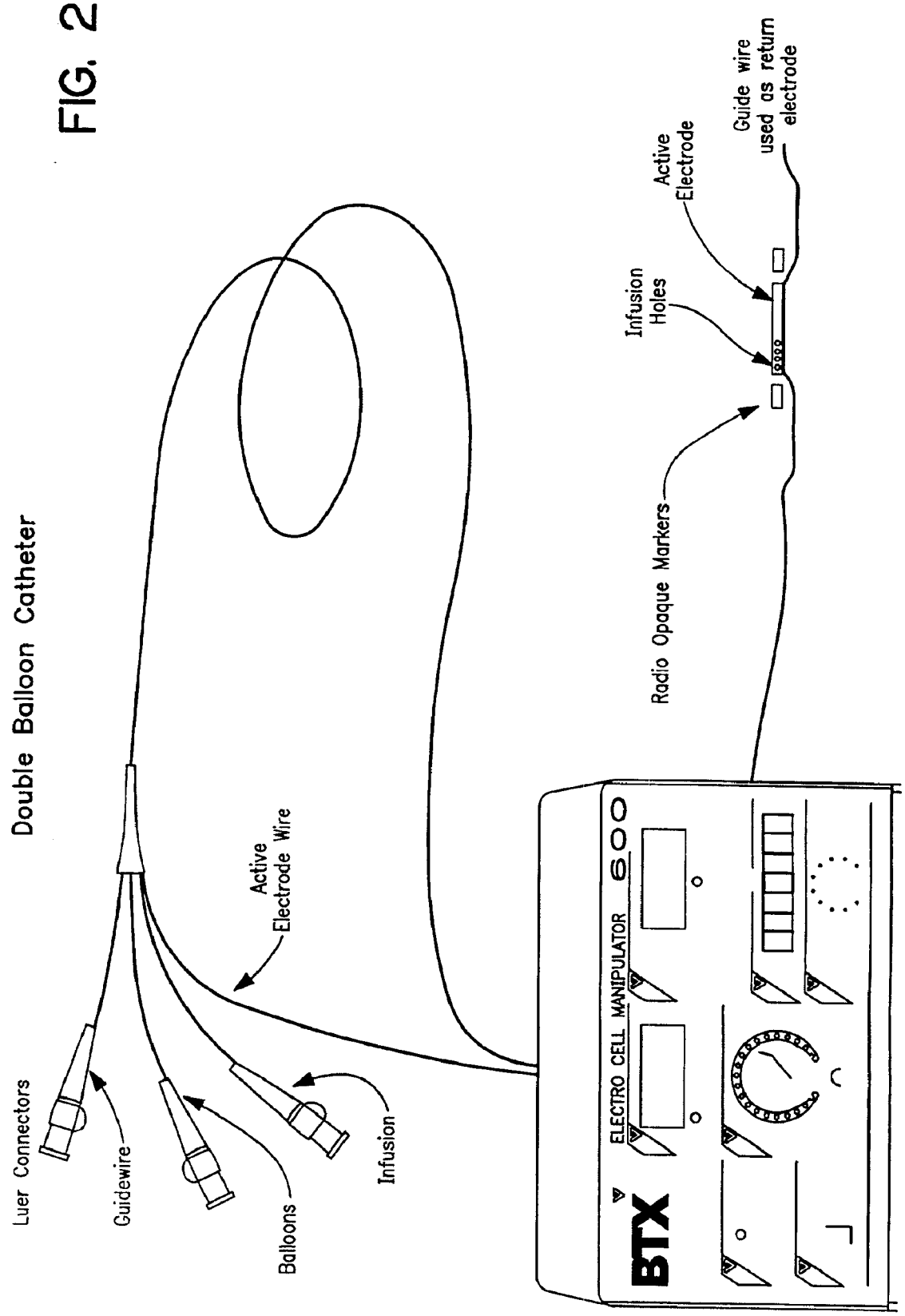
FIG. 2 is a schematic diagram of an exemplary endoluminal balloon electroporation catheter in which the guidewire for inserting the catheter serves as the return electrode.
Figure 3:
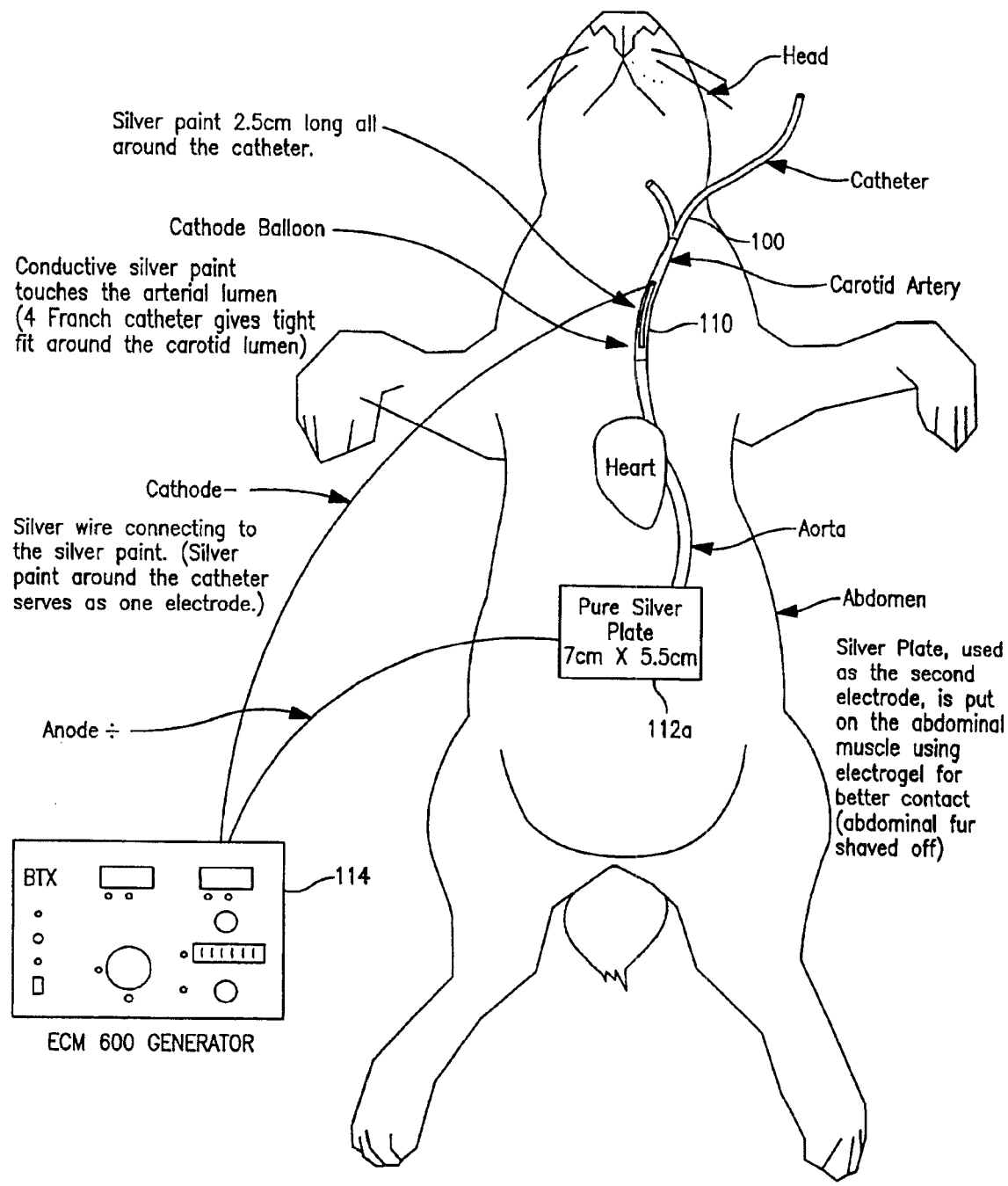
FIG. 3 is a schematic diagram of a rabbit treated by a method of the invention, including several of the elements of an exemplary catheter apparatus in which one electrode is within the vessel lumen and the other electrode is in contact with the body surface.
Figure 4:
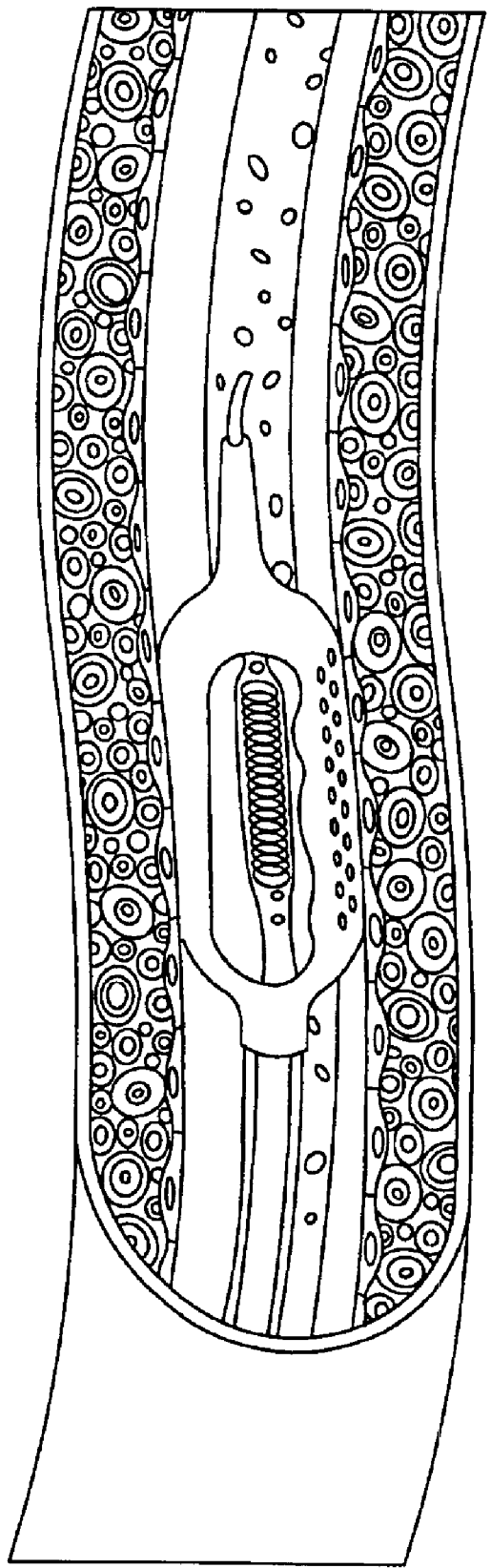
FIG. 4 is a schematic diagram of an electroporation catheter having a balloon that is porous.

Catheters (e.g., balloon type) having various balloon sizes suitable for endoluminal use in a variety of vessel types and sizes (e.g., blood vessels, large and small intestine, urethra, etc.) are commercially available. Such commercially available catheters can be modified to include electrodes suitable for applying an electrical impulse. The catheter may be, for example, a modified Berman catheter (Arrow International, Inc., Reading, Pa.). One of skill in the art will know of other catheter devices that can be modified for endoluminal electropulsing based on the teachings herein. Exemplary endoluminal catheter devices useful in the methods of the invention are modified as described herein, and are shown in FIGS. 1 to 3. FIG. 4 shows a porous balloon catheter having multiple holes on the balloon surface and a guidewire positioned within the balloon shaft which serves as the electrode. The holes can be used to optionally administer compositions into the vessel.

A catheter 100 (FIG. 1) includes at least one inflatable balloon 102 near the distal end of the catheter 100, and at least one inflation port 104 for inflating the at least one inflatable balloon 102, in a conventional manner. The catheter 100 also includes a first electrode 110 and a second electrode 112 that are coupled by wires to a voltage source generator 114, which may be, for example, an ECM 600 exponential pulse generator (BTX, a division of Genetronics, Inc., San Diego, Calif.).

In one embodiment, the catheter 100 has at least one infusion port for introducing a composition into a vessel of the subject. As used herein, the term "infusion port" refers to a part of an apparatus that is capable of introducing a composition, such as a drug (e.g., heparin), via infusion. Infusion openings 120 capable of delivering the introduced composition endoluminally can be made during or after manufacture of the catheter 100, and can be placed on one or both sides of the first electrode 110, or within the bounds of the first electrode 110. The first electrode 110 is preferably placed close to the at least one infusion opening 120. In one embodiment, the infusion openings 120 may be coincident with the first electrode 110, such that the first electrode 110 completely surrounds the at least one infusion opening 120.

The first electrode 110 is preferably made of an electrically conductive material that is biologically compatible, e.g., biologically inert, with a subject. Examples of such material include silver or platinum wire wrapped around or laid on or near the surface of the catheter 100; a plated or painted coating of conductive material, such as silver paint, on some portion of the catheter 100; or a region of the catheter 100 that has been made conductive by implantation (during or after manufacture, such as by ion implantation) of electrically conductive materials, such as powdered metal or conductive fibers. The conductor need not be limited to metal, but can be a conductive plastic or ceramic. For ease of manufacture, the embodiments shown in FIGS. 1 and 3 use conductive silver paint for the first electrode 110 as a coating on approximately 2.5 cm of the length of the catheter 100 near the infusion openings 120.

The second electrode 112 (FIG. 1) similarly comprises an electrically conductive material, and can be of the same or different type of conductive material as the first electrode 110. The second electrode 112 maybe formed in a manner similar to the first electrode 110 and positioned between the first electrode 110 and the infusion openings 120, or positioned with the infusion openings 120 between the first electrode 110 and the second electrode 112 (FIG. 1). Other configurations of the first electrode 110 and the second electrode 112 can be utilized, such as interdigitated electrodes with infusion openings 120 nearby or between the interdigitated "fingers" of the electrodes, or as concentric rings with the infusion openings within the centermost ring, between the centermost and outermost ring, or outside of the outermost ring. Additional catheter configurations are within the scope of the present invention so long as they provide a structure that, when supplied by voltage from the voltage source 114, generates an electric field sufficient to induce the vasodilation of a vessel or to increase the flow of fluid through a vessel.

The first electrode 110 and the second electrode 112 are coupled to the voltage source 114 by conductors, which may be, for example, silver or platinum wires, but can be any conductive structure, such as flexible conductive ink within the catheter 100 for connecting the first electrode 110.

In an alternative embodiment shown in FIG. 3, the second electrode comprises a silver plate 112a configured to be applied to a portion of the body of a subject such that an electric field sufficient to induce vessel vasodilation or to increase the flow of fluid through a vessel is generated when voltage from the voltage source 114 is applied to the first electrode 110 and the second electrode 112a. The second electrode, when placed externally, is preferably placed on bare skin (e.g., shaved abdominal muscle of the subject), preferably using a conductive gel for better contact.

In operation, the catheter 100 is inserted into a vessel (e.g., an artery or vein) endoluminally and is positioned so that a balloon 102 traverses or crosses the vessel region to be pulsed. The balloon 102 is then inflated to expand the vessel, if desired, and a electrical pulse from the voltage source 114 is applied to the first electrode 110 and second electrode 112 so as to induce the vasodilation of the vessel or increase the flow of fluid through the vessel. If desired, a composition is administered into the vessel via the infusion openings 120, at some point in time before, during, or after applying an electrical pulse or between electrical pulses.

Thus, in another embodiment, the invention provides a method for inducing the vasodilation of a vessel in a subject by applying an electrical impulse to the vessel using a catheter apparatus having at least one inflatable balloon portion, a first electrode, a second electrode positioned with respect to the first electrode and the subject such that an electric field sufficient to induce vasodilation of the vessel is generated by the electrical impulse, wherein application of the electrical impulse induces vasodilation of the vessel.

In one aspect of this embodiment, the methods of the invention employ a modified electroporation catheter apparatus having a double balloon configuration, as illustrated in FIG. 2 (Danforth Biomedical, Calif.). The double balloon catheter contains two 2.5 mm PET balloons of about 10 mm in length each with radio-opaque markers mounted on a catheter shaft of about 1 mm in diameter and about 60 cm in length. The balloons are separated by a space of about 20 mm. Both balloons can be infusion lumen of the catheter. An active electrode of about 7 mm in length is tightly wrapped around the infusion outlet holes, which connects via a lumen to an external power supply. In this aspect, a clinical 0.014 inch guidewire through the guidewire lumen of the catheter serves as a return electrode. In operation, both electrodes of the EPC are within the vessel lumen, the electrodes are positioned near where the electrical pulse is to be applied, and the voltage applied between the first and second electrode is of sufficient strength and duration to induce the vasodilation of the vessel or to increase the flow of fluid through the vessel.

Pulse generators useful for delivering the electrical pulses are commercially available. For example, a pulse generator such as the ECM Model 600 (BTX, a division of Genetronics, Inc., San Diego, Calif.) can be used to practice the methods of the invention (FIG. 1). The ECM 600 generates an electric pulse from the complete discharge of a capacitor is characterized by a fast rise time and an exponentially decaying waveform tail. In the ECM 600, the pulse length is set by selecting one of ten timing resistors marked R1 through R10. They are active in both High Voltage Mode (HVM) (capacitance fixed at fifty microfarads) and Low Voltage Mode (LVM) (with a capacitance range from 25 to 3,175 microfarads).

The ECM 600 pulse generator has a control knob that permits the adjustment of the amplitude of the set charging voltage applied to the internal capacitors from 50 to 500 volts in LVM and from 0.05 to 2.5 kV in the HVM; the maximum amplitude of the electrical pulse is shown on a display. This device further includes a plurality of push button switches for controlling pulse length, in the LVM mode, by a simultaneous combination of resistors parallel to the output and a bank of seven selectable additive capacitors.

The ECM 600 also includes a single automatic charge and pulse push button. This button may be depressed to initiate both charging of the internal capacitors to the set voltage and to deliver a pulse to the outside electrodes in an automatic cycle that takes less than five seconds. If desired, the manual button may be pressed repeatedly to apply multiple electric pulses to the vessel.

The ECM 600 provides the voltage (in Volts) that travels across the gap (in cm) between the electrodes. This potential difference defines what is called the electric field strength where E equals Volts/cm. Thus, the distance between the electrodes can be measured and a suitable voltage according to the formula E=V/d can then be applied to the electrodes (E=electric field strength in V/cm; V=voltage in volts; and d=distance in cm). The waveforms of the pulse provided by the ECM600 in the power pack deliver an exponentially decaying pulse.

It is understood that other pulse generating systems can be utilized in the methods of the invention. For example, the ElectroSquarePorator (T820) can be used to apply a square wave pulse to a vessel, if desired (Genetronics, Inc., San Diego, Calif.). Square wave electrical pulses rise quickly to the set voltage and stay at that level for a set length of time (pulse length) and then rapidly decay to zero. This type of electrical pulse is preferred where a composition is to be delivered into cells via electroporation, as discussed below.

The T820 is capable of generating up to 3000 volts. The pulse length is adjustable from 5 $\mu$s to 99 msec. The T820 is active in both High Voltage Mode (100 to 3000 volts) and Low Voltage Mode (10 to 500 volts) and has multiple pulsing capability (1 to 99 pulses).

The methods of the invention for inducing or increasing vasodilation of a vessel in a subject are useful in treating clinical situations in which a subject exhibits a blockage, undesirable narrowing or a situation in which it is desired to dilate a vessel. Thus, a method of the invention can be used to treat vessel blockages or narrowing caused by events that occur within the vessel, for example, the luminal renarrowing that occurs within an artery during restenosis or that occurs as a result of a blood clot.

A method of the invention also can be used to treat vessel blockage or narrowing caused by events that occur external to the vessel, for example, where an external mass, such as a tumor, causes vessel constriction or blockage as a result of pressure. Tumor masses often cause the obstruction or blockage of the gastrointestinal system or blood vessels that supply blood to one or more vital organs and therefore, obstruction or blockage can be treated by using a method of the invention. Prostate hyperplasia, which often causes urethra constriction or obstruction, is another example of a clinical situation that can be treated with a method of the invention. Such constrictions or blockages can lead to severe discomfort, organ failure, or an inability to consume food. Accordingly, the methods of the invention also can be useful for relieving the symptoms associated with vessel obstruction or blockage caused by an external mass or other form of external pressure (e.g., pain, inability to consume food, difficult or frequent urination, etc.).

The methods of the invention for inducing or increasing the flow of fluid through a vessel in a subject are useful in treating clinical situations for which a blockage or an undesirable decrease in the flow of fluid through a vessel occurs, or for situations in which it is desired to induce or increase the flow of fluid through a vessel. For example, the above-described obstructions or blockages can be treated. The invention methods for inducing or increasing the flow of fluid through a vessel can be used to treat various clinical situations, for example, an artery which supplies blood to the heart in which a blockage, narrowing or occlusion is present in the artery, such as that caused by restenosis or a blood clot. Acute or chronic angina, which can be caused by a lack of oxygen to the heart, can be treated. Additionally, a vessel supplying blood to a transplanted organ in which it is desired to induce or increase the delivery of nutrients or oxygen to the transplanted organ can be treated. Similarly, a blood vessel that supplies blood to a tumorous organ can be treated in order to induce or increase delivery of a chemotherapeutic agent more efficiently to the afflicted organ.

In another embodiment, a composition is administered to the vessel in the subject prior to, substantially contemporaneously with or after the application of the electrical impulse. In one aspect, an electrical impulse is of the appropriate strength and duration to electroporate at least one cell thereby allowing the composition to be delivered into the at least one electroporated cell.

As used herein, the term "substantially contemporaneously" means that the composition is administered and the electrical pulse is applied reasonably close together in time. Preferably, the composition is administered concurrently with electropulsing, or at some point in time before electropulsing. Thus, in another embodiment the composition is administered either prior to or substantially contemporaneously with the application of the electropulse. When applying multiple electrical impulses, the composition can be administered before or after each of the pulses, or at any time between the electrical pulses.

In another embodiment, the composition is delivered locally. As used herein, the term "local" means in a confined or in a particular region. Thus, the term "local" when used in reference to the delivery of a composition means that the composition remains near the delivery site. The skilled artisan will recognize that a composition delivered locally can, over time, be distributed throughout a subject depending on various factors, for example, the concentration of the composition, the half-life of the composition, the site of delivery, the efficiency of cell electroporation and the degree of leakage from the delivery site that occurs, for example, as a result of the porosity of the vessel into which the composition is delivered. The localized delivery of compositions to cells of a vessel in a subject via electroporation is described in U.S. application Ser. No. 08/668,725, which is herein incorporated by reference.

Vasoconstrictor agents or mechanical devices can be used to keep the therapeutic composition localized prior to, during or after pulsing. For example, a catheter apparatus having a double balloon configuration can hold the composition in place between the two balloons for localized delivery (see for example, FIG. 1).

In another embodiment, the composition is delivered systemically. As used herein, the term "systemic" means throughout the body of the subject. Thus, a composition that is delivered systemically is generally present throughout the body. A composition delivered systemically can be followed by pulsing at a vessel blockage or narrowing in order to deliver the compositions into the site, for example.

The chemical structure of the composition, its intended function and the preparation administered will dictate the most appropriate time to administer the composition in relation to applying the electrical pulse. Such factors include, for example, the particular clinical situation, the condition of the patient, the size of the composition, the presence of a carrier and the half-life of the composition. One skilled in the art, depending on the desired effect of the electrical pulsing and an administered composition can readily determine when the composition should be administered in relationship to applying the electrical impulse.

Administration of the composition prior to or substantially contemporaneously with an electrical impulse applied via electroporation allows the composition to enter at least one electroporated cell. The at least one electroporated cell will generally be near the region at which the electrical impulse is applied, i.e., in the vessel cavity (e.g., blood) or in the vessel wall. For example, in a blood vessel, the composition can be delivered into the tunica intima, tunica media or tunica adventitia of the vessel. One skilled in the art will readily recognize that although the terms "tunica intima," "tunica media" and "tunica adventitia" are used in the art of cardiology to refer to the increasing depth of a blood vessel wall as measured from the lumen, that compositions can be delivered into the vessel wall of other vessels (e.g., lymph vessel, G.I. vessel etc.) at depths corresponding to the tunica intima, tunica media and tunica adventitia.

The compositions delivered into the at least one electroporated cell can be retained by the electroporated cell thereby resulting in sustained delivery of the composition. As used herein, the term "sustained" refers to the presence of the composition over a relatively prolonged period of time during which there is no appreciable washout. In general, "sustained" delivery of a composition means that the composition is present for about 12 hours, but can be longer, for example, steadily over 24 to 72 hours. Sustained delivery generally means that the compositions are present for a longer period of time than if the composition were delivered by conventional methods (e.g., by injection into the bloodstream). In the case of genes, for example, gene expression can last for several weeks.

Figure 8:
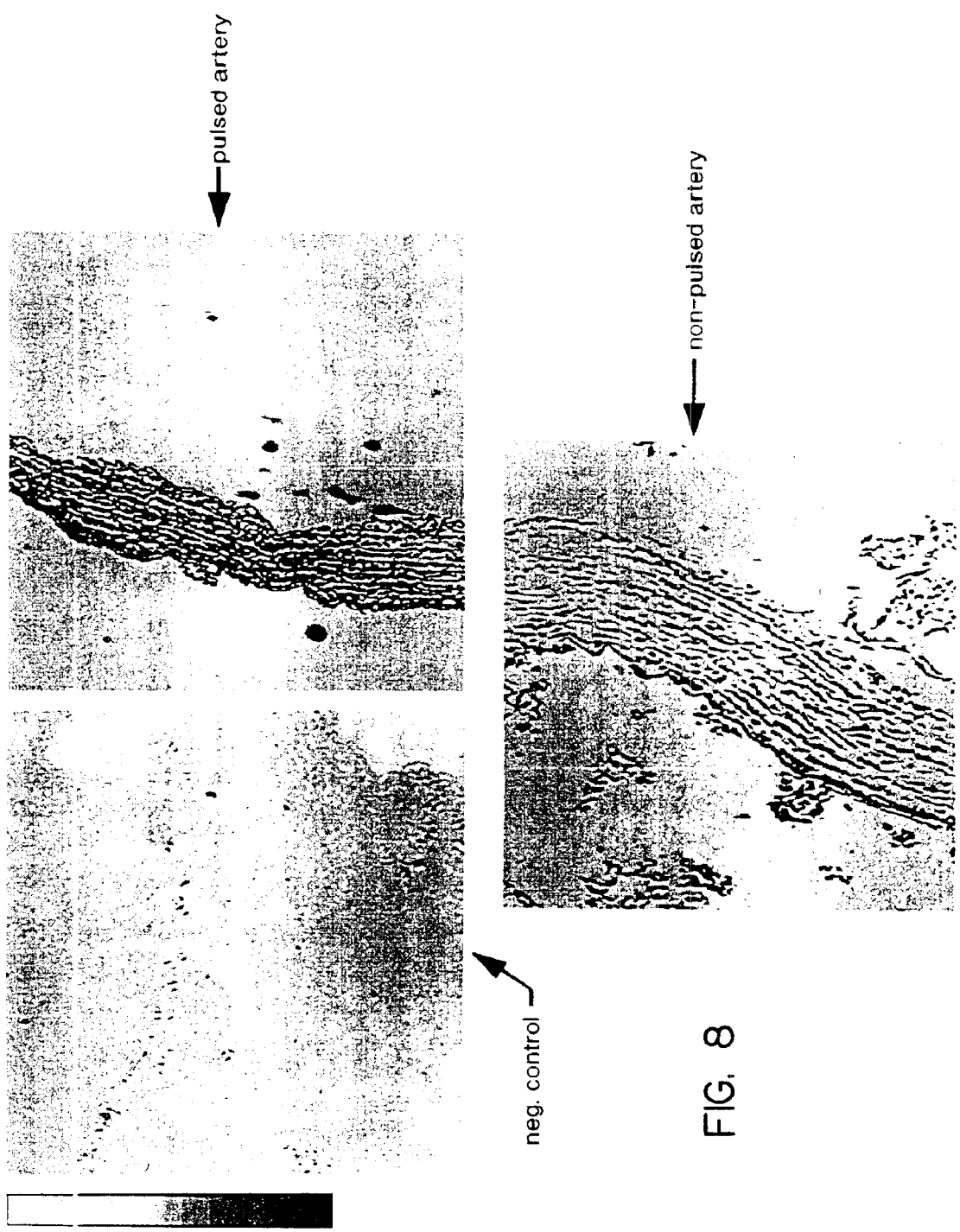
FIG. 8 shows the uptake of heparin in the arterial tissue after applying the electrical pulse. The upper left panel is without heparin and without electropulsing, the upper right panel is with heparin and with electropulsing and the bottom panel is with heparin but without electropulsing. The relative color intensity increases from top (lightest) to bottom (darkest) in the color ladder. Arteries receiving heparin received 10 units/Kg heparin locally, and arteries were excised four hours after treatment in which the guidewire for inserting the catheter serves as the return electrode.

As disclosed herein (e.g., Example III), a double-balloon catheter system incorporating electroporation technology was used to deliver heparin into a vessel in an overstretch balloon injury animal model. Following arterial injury, the double-balloon catheter was inserted endoluminally, fluoresceinated heparin was administered into the space between the two inflated balloons, and the artery was subjected to an electrical pulse. Catheter deployment and endoluminal electrical pulsing were well tolerated in all animals (N=21) without adverse hemodynamic and histological changes. Periodic arterial blood samples revealed no abnormalities in the clotting profile or any gross morphological changes in the blood cells up to 8 hours after treatment. Histochemical staining of the tissue showed intracellular localization of heparin (FIGS. 7 and 8). Furthermore, heparin fluorescence was detected throughout the vessel layers in the pulsed arteries for at least 12 hours in comparison to the unpulsed control.

It is contemplated that the electropulsing parameters can be manipulated in order to modulate the delivery of a composition into particular areas of a vessel. It is further contemplated that the electropulsing parameters can be manipulated as appropriate in order to deliver a composition beyond the exterior vessel wall, i.e., into a tissue or space that surrounds a vessel.

As used herein, the term "modulate," when used in reference to the delivery of a composition, means to control or to regulate the area of the vessel into which the composition is delivered. For example, where it is desired to deliver a composition into cells at the luminal surface of a vessel (i.e., the tunica intima), an impulse having a particular strength and duration can be applied to the vessel. Where delivery of a composition into the tunica media or into the tunica adventitia is desired, an impulse having a greater strength, duration or multiple pulses will be applied to the vessel. Delivery of a composition into a stenotic lesion can similarly be achieved by increasing pulse number, strength or duration. Denuding the vessel prior to electropulsing can also be used to modulate delivery of a composition. For example, denuding blood vessel epithelium prior to applying the electrical pulse facilitated the delivery of heparin into deeper areas of the blood vessel, such as into the tunica media and into the tunica adventitia (FIGS. 7 and 8).

Compositions contemplated for use in the methods of the invention include those that elicit a biological effect or response such as drugs (e.g., vessel vasodilators, cell proliferation inhibitors, anticancer agents, angioproliferative inhibitors, antibiotics, antiviral agents, fungicides and antimycobacterial agents), polynucleotides (e.g., genes used in gene therapy, antisense nucleotides, ribozymes), polypeptides (e.g., proteins, antibodies, fragments thereof, functional derivatives thereof including, for example, protease resistant analogues). Additional useful compositions include dyes, stains, radionuclides (e.g., barium), luminescent and fluorescent agents (e.g., fluorescein), and other compositions (e.g., gold particles) for the visualization of a vessel cavity or vessel lumen, or for the visualization of a tissue or space that surrounds a vessel.

Administering a composition that induces or increases vessel vasodilation or that induces or increases the flow of fluid through a vessel in combination with electropulsing can provide an additive or synergistic effect. Compositions known to induce or increase vessel vasodilation or induce or increase the flow of fluid through a vessel are therefore particularly useful in treating various clinical situations characterized by undesirable vessel narrowing, such as restenosis, as described further below. Specific examples of such compositions include, for example, high and low molecular weight heparin and fragments thereof, which may control post-PTCA vascular renarrowing caused by intimal thickening and hyperplasia. Heparin also facilitates blood flow, modulates some growth factors and provides cytoprotective action (Black et al., *Cardiovas. Res.* 29:629–636 (1995)) and has an inhibitory effect on smooth muscle, Schwann and epithelial cell proliferation in vitro (Clowes et al., *Circ. Res.* 58:839–845 (1986)), U-937 leukemia cell proliferation (Volpi et al., *Exp. Cell. Res.* 215:119–130 (1994)) and on thrombogenicity (Araki et al., *Circ. Res.* 71:577–584 (1992)).

Additional examples of preferred compositions include antithrombotic, antirestenotic, antiplatelet, and antiproliferative compositions, for example, platelet receptor and mediator inhibitors, smooth muscle cell proliferation inhibitors, growth factor inhibitors, GpIIb/IIIa antagonists, cell adhesion and aggregation inhibitors (e.g., platelet adhesion and aggregation), PDGF inhibitors, matrix synthesis inhibitors, thromboxane receptor inhibitors, fibrinogen receptor inhibitors, serotonin inhibitors, fibrosis inhibitors and the like.

Thus, in another embodiment, the composition that is administered to the vessel inhibits cell proliferation. In one aspect, the cell proliferation inhibited is associated with vessel intimal thickening or hyperplasia.

Particular useful compositions therefore, include angiotensin converting enzyme (ACE) inhibitors, colchicine, somatostatin analogues, hirudin, hirulog, tissue plasminogen activator (tPA), urokinase, streptokinase, warfarin, PDGF-antibodies, proteases such as elastase and collagenase, serotonin, prostaglandins, vasoconstrictors, vasodilators, anti-angiogenesis factors, Factor VII or Factor IX, TNF, tissue factor, VLA-4, gax, L-arginine, GR32191, sulotroban, ketanserin, fish oil, enoxaprin, cilazapril, forinopril, lovastatin, angiopeptin, cyclosporin A, steroids, trapidil, colchicine, DMSO, retinoids, thrombin inhibitors, antibodies to von Willebrand factor, antibodies to glycoprotein IIb/IIIa and calcium chelating agents, for example.

Anticancer or chemotherapeutic drugs having an antitumor or cyotoxic effect also are useful compositions. Anticancer drugs include, for example, cell proliferation, angiogenesis and metastases inhibitors (e.g., cell attachment inhibitors), as well as inducers or promoters of apoptosis, growth arrest and the like. Chemotherapeutic drugs include, for example, bleomycin, cisplatin, 5-fluorouracil, doxorubicin, taxol, suramin, neocarcinostatin. Other compositions known in the art are applicable in the methods of the invention (e.g., Remington's Pharmaceutical Sciences, 18th ed., Mack Publishing Co., Easton, Pa., 1990; The Merck Index, 12th ed., Merck Publishing Group, Whitehouse, N.J., 1996, which are herein incorporated by reference).

Polynucleotides useful in the methods of the invention include DNA, cDNA, RNA, and oligonucleotides thereof, either unmodified or modified (e.g., nuclease resistant forms, conjugated forms, e.g., to beads or to biotin and the like). Such polynucleotides can encode proteins or polypeptides that inhibit or induce cell proliferation (e.g., growth-arrest homeobox gene), or angioproliferation, or have antithrombotic, antirestenotic, antiplatelet, antifibrotic or anticancer activity. Preferred polynucleotides function additively or synergistically for inducing vessel vasodilation or for increasing the flow of fluid through a vessel.

Antisense polynucleotides complementary to RNA molecules (e.g., mRNA) that promote or inhibit the above-described activities (cell proliferation, adhesion, clotting, angioproliferation, fibrosis etc.) also are contemplated for use. Although not wishing to be bound by a particular theory, it is believed that antisense molecules hybridize to a complementary mRNA in the cell thereby inhibiting translation of the mRNA. Preferred antisense oligonucleotides are about 15 to 30 base pairs to minimize the possibility of the antisense forming an internal secondary structure. Oligonucleotides that form triplexes with double-helical DNA can be used where it is desired to inhibit transcription of a particular DNA sequence in cells. Such triplex oligonucleotides can be designed to recognize a unique site on a chosen gene, for example (Maher et al., *Antisense Res. and Dev.* 1:227 (1991); Helene, *Anticancer Drug Design* 6:569 (1991)).

Ribozymes are RNA molecules that have the ability to cleave other single-stranded RNA molecules at particular nucleotide sites. Thus, it is possible to engineer ribozymes for the purpose of cleaving specific RNA molecules which have the nucleotide sequences cleaved (Czech, *J. Amer. Med. Assn.* 260:3030 (1988)). Only those RNA molecules having the particular nucleotide sites will be cleaved and subsequently inactivated. As the hammerhead-type of ribozymes have longer recognition motifs (11 to 18 base pairs) than tetrahymena-type ribozymes (four base pairs), hammerhead-types are preferably used for inactivating particular RNA molecules.

The polynucleotides of the invention can, if desired, be naked or be contained in a vector (e.g., retroviral vector, adenoviral vectors and the like), in a carrier (e.g., DNA-liposome complex), or conjugated to inert beads or other functional moieties (e.g., biotin, streptavidin, lectins, etc.), or appropriate compositions disclosed herein. Such polynucleotides can be modified, for example, to be resistant to nucleases. Thus, both viral and non-viral means of polynucleotide delivery can be achieved and are contemplated using the methods of the invention.

Modified compositions that are biologically functional analogues of the compositions described herein also are useful in the methods of the invention. Such modified compositions can have sulfate groups, phosphate groups, or hydrophobic groups such as aliphatic or aromatic aglycones added or removed. For example, modified heparin can include the addition of non-heparin saccharide residues such as sialic acid, galactose, fucose, glucose, and xylose. When heparin is used as the composition, it may include a fragment of naturally occurring heparin or heparin-like molecule such as heparin sulfate or other glycosaminoglycans, or may be synthetic fragments. The synthetic fragments could be modified in saccharide linkage in order to produce more effective blockers of selecting binding. Methods for producing such saccharides will be known by those of skill in the art (see for example, M. Petitou, Chemical Synthesis of Heparin, in *Heparin, Chemical and Biological Properties.*

*Clinical Applications*, CRC Press, Boca Raton, Fla., D. A. Lane and V. Lindahl, eds., 1989, pp. 65–79).

The compositions administered by a method of the invention can be administered parenterally by injection or by gradual perfusion over time. The composition can be administered intravenously, intraperitoneally, intramuscularly, subcutaneously, intracavity, or transdermally, and preferably is administered intravascularly at or near the site of electroporation. Compositions also can be administered with a catheter apparatus having at least one infusion port for introducing the composition into the vessel.

The compositions administered will be in a "pharmaceutically acceptable" or "physiologically acceptable" preparation. As used herein, the terms "pharmaceutically acceptable" and "physiologically acceptable" refer to carriers, diluents, excipients and the like that can be administered to a subject, preferably without excessive adverse side effects (e.g., nausea, headaches, etc.).

Such preparations for administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobial, anti-oxidants, chelating agents, and inert gases and the like.

Controlling the duration of action or controlled delivery of an administered composition can be achieved by incorporating the composition into particles or a polymeric substance such as polyesters, polyamine acids, hydrogel, polyvinyl pyrrolidone, ethylene-vinylacetate, methylcellulose, carboxymethylcellulose, protamine sulfate, or lactide/glycolide copolymers, polylactide/glycolide copolymers, or ethylenevinylacetate copolymers. The rate of release of the composition may be controlled by altering the concentration or composition of such macromolecules.

For example, it is possible to entrap a composition in micro-capsules prepared by coacervation techniques or by interfacial polymerization, for example, by the use of hydroxymethylcellulose or gelatin-microcapsules or poly (methylmethacrolate) microcapsules, respectively, or in a colloid drug delivery system. Colloidal dispersion systems include macromolecule complexes, nano-capsules, microspheres, beads, and lipid-based systems including oil-in-water emulsions, micelles, mixed micelles, and liposomes.

The above-described compositions and others not specifically described herein are useful in various clinical situations and can be administered alone, or in a combination with other compositions by a method of the invention. The compositions administered alone, or in combination include combinations of tPA, urokinase, prourokinase, heparin, and streptokinase, for example. Administration of heparin with tissue plasminogen activator would reduce the dose of tissue plasminogen activator that would be required, thereby reducing the risk of clot formation which is often associated with the conclusion of tissue plasminogen activator and other thrombolytic or fibrinolytic therapies. Further, compositions containing heparin may include a mixture of molecules containing from about 2 to about 50 saccharide units or may be homogeneous fragments as long as the number of saccharide units is 2 or more, but not greater than about 50.

Preferred clinical situations which can be treated using a method of the invention include but are not limited to: 1) acute arterial thrombotic occlusion including coronary, cerebral or peripheral arteries; 2) acute thrombotic occlusion or restenosis after angioplasty; 3) reocclusion or restenosis after thrombolytic therapy (e.g., in an ishemic tissue); 4) vascular graft occlusion; 5) hemodialysis; 6) cardiopulmonary bypass surgery; 7) left ventricular cardiac assist device; 8) total artificial heart and left ventricular assist devices; 9) septic shock; 10) other arterial thromboses (e.g., thrombolism where current therapeutic measures are either contraindicated or ineffective).

Alternatively, various nucleic acid sequences encoding a protein of interest can be used for treatment of cardiovascular disorders. In particular, the expression of the growth factors PDGF-B, FGF-1 and TGFβ1 has been associated with intimal hyperplasia. Thus, either increasing (deliver sense constructs) or decreasing (deliver antisense constructs) such gene expression can be useful in treating such disorders. For example, whereas PDGF-B is associated with smooth muscle cell (SMC) proliferation and migration, FGF-1 stimulates angiogenesis and TGF β1 accelerates procollagen synthesis. Thus, a nucleic acid that encodes an inhibitor of SMC proliferation, migration, platelet aggregation, extracellular remodeling or matrix formation also is desirable for use in the methods of the invention. Such compositions further include interferon-γ, which inhibits proliferation and expression of a-smooth muscle actin in arterial SMCs and non-protein mediators such as prostaglandin of the E series.

Examples of other genes to be delivered by a method of the invention include vascular endothelial growth factor (VEGF) and endothelial specific mitogen, which can stimulate angiogenesis and regulate both physiologic and pathologic angiogenesis.

Administration of the composition by a method of the invention can be used for ameliorating post-reperfusion injury, for example. When treating arterial thrombosis, induction of reperfusion by clot lysing agents such as tPA is often associated with tissue damage.

The methods of the invention also are useful for delivering compositions that inhibit microbial infection which can be useful in the treatment of microbial infections. Many microbes, such as bacteria, rickettsia, various parasites, and viruses, bind to vascular endothelium and leukocytes. Thus, the methods of the invention may be used to deliver a composition to a patient to prevent binding of a microbe which uses a particular receptor (e.g., selectin) as its binding target molecule, thereby inhibiting or reducing the microbial infection.

The methods of the invention can be used to treat vasculitis by administering a composition described above to a patient. Tissue damage associated with focal adhesion of leukocytes to the endothelial lining of blood vessels is inhibited by blocking the P-selectin and L-selectin receptors, for example.

The doses needed for clinical efficacy of the administered compositions are those large enough to produce a desired effect in which the signs or symptoms of the clinical situation are ameliorated. The dose should not be so large as to cause excessive adverse side effects. Generally, the dose will vary with the age, condition, sex and extent of the disease in the patient and can be determined by one of skill in the art. The dose can be adjusted by the individual physician in the event of any complication. When used for the treatment of inflammation, post-reperfusion injury, microbial/viral infection, or vasculitis, or inhibition of the metastatic spread of tumor cells, for example, the composition may be administered at a dose which can vary from about 1 mg/Kg to about 1000 mg/Kg, preferably about 1 mg/Kg to about 50 mg/Kg, in one or more dose administrations.

The following examples are intended to illustrate but not limit the invention. While they are typical of those that might be used, other procedures and applications of the invention methods known to those skilled in the art may alternatively be used.

EXAMPLE I

This example describes applying an electrical impulse to a vessel in a subject.

Animal Preparation and Surgical Approach:

This study conformed to the care and use of laboratory animals and standard euthanasia procedures policies by the NIH guide set forth in the Institutional Animal Care and Use Committee, and to the position of the American Heart Association on Research Animal Use. New Zealand White rabbits weighing 3.2–4.2 kg of both sexes (N=21) were utilized in the studies. After withdrawal of food for 12–18 hrs, but not water, the animals were sedated using 2 mg/Kg intramuscular xylazine (Miles Inc., KS) and 50 mg/Kg ketamine (Fort Dodge Lab, IA). Sedated animals were anesthetized with 30 mg/Kg α-chloralose (Fisher Scientific, NJ) throughout the ear vein and endotracheally intubated. Once anesthetized, the animal was strapped supine on the surgical table and ventilated with a volume controlled Harvard 665 ventilator (Harvard Apparatus, Natick, Ma.). Corneal and toe-pinching reflexes monitored the state of anesthesia. A supplemental dose of α-chloralose (10 mg/Kg every hour) was injected intravenously for adequate anesthesia. Throughout the experimental procedure, $pO_2$ and $pCO_2$ were maintained at physiological levels and the body temperature was maintained at 37° C. using an infrared heating lamp or thermostatic blanket. A polyethylene cannula connected to a pressure transducer (Statham P23Db) was introduced into a femoral artery for continuous monitoring (DC-300 Hz) of systemic blood pressure. EKG monitoring (0.05 Hz-1 KHz) was undertaken using Lead I or Lead II connected to a differential amplifier. Expiratory $CO_2$ was monitored with a respiratory $CO_2$ analyzer (223 Puritan-Bennett). Blood pressure, EKG and end-tidal $CO_2$ signals were suitably amplified and output signals fed in parallel to a storage oscilloscope (Tektronix, Oreg.) and to an analog chart recorder (Gould, Ohio).

The common carotid arteries (CCA) of the animals were accessed either by making a midline incision in the cervical region and isolating them from the surrounding vago-sympathetic trunk (N=16) or through the femoral artery under fluoroscopic guidance (N=5).

Catheterization Procedure and Experimental Protocol:

I) Retrograde approach: A small vascular clip was applied onto the caudal end of one common carotid artery (CCA), and the catheter was pushed up to the junction of the CCA and the innominate artery through a small incision at the rostral end of the CCA. The balloons were next inflated to 2–3 atm inside the carotid lumen, rubbed and pulled against the length of the CCA for 45 to 60 seconds to denude the endothelium of the artery. Following this, the balloons were inflated at 4 atm to keep the lumen occluded during the intervention period. Fluoresceinated heparin (F-heparin; Molecular Probes, OR) at a dose of 8 to 30 units/Kg was delivered over a period of 30 seconds through the infusion lumen of the catheter. Immediately after the introduction of F-heparin the catheter electrodes were connected to an ECM 600 exponential pulse generator (BTX, San Diego, Calif.) and four pulses varying from 63 to 90 volts having a pulse width of 7.0 to 9.65 msec in different experiments were applied endoluminally over a period of approximately 60 to 90 seconds. Following electropulsing, the balloons were deflated, the catheter was withdrawn and the incised rostral end of the artery was ligated or an arterial repair was made and the vascular clip was taken off to restore cranial blood flow. The contralateral artery received the same treatment, but no electropulsing.

II) Antgrade approach: Under fluoroscopy the EPC was inserted into the femoral artery through a 5 F arterial sheath (Cook, Inc., IN). It was first passed into one CCA and then partially withdrawn and passed into the contralateral CCA. Drug delivery and electropulsing were performed as described above for the retrograde approach.

Tissue Processing:

Between 1 to 12 hours after pulsing, the animal was sacrificed. The carotid arteries were quickly excised, embedded in optimum cutting temperature compound (OCT), and frozen in isopentane dipped in liquid nitrogen. Serial sections (10 to 15 microns in thickness) of the tissue were prepared using a Reichert-Jung microtome. Frozen tissue sections mounted in glycerol were viewed with a confocal laser scanning or epifluorescence microscope (Zeiss Axiovert) connected to a Hamamatsu CCD camera and Argus image processor. The image signal was fed into a video monitor and stored in an optical disk for further processing and analysis using NIH image analysis software. Some tissues were dipped in formalin for 24 to 36 hours and paraffin embedded. Serial sections (10 to 15 microns in thickness) stained with hematoxylin-eosin (H-E) or van Giesson were observed by light microscopy for any evidence of gross tissue damage.

Safety Data:

Blood Pressure

Intravascular pulsing of CCA had no influence on systemic arterial pressure monitored throughout the studies, except that each pulse in the stimulation sequence caused a very transient reduction of the mean arterial pressure in the range of 5 to 20 torr, which immediately returned to baseline levels on cessation of pulsing stimuli.

Electrocardiogram

Randomly induced impulse given at different phases of the cardiac did not change the prepulsing lead II EKG pattern. There was no appreciable change in heart rate nor did the pulsing elicit any arrhythmia or atrial/ventricular fibrillation. No deviation from the normal P-R interval (0.05 to 0.08 sec) on pulsed stimuli was noticed, suggesting that intraluminal pulsing did not evoke any atrioventricular conduction defect.

Blood Chemistry and Morphology

Prothrombin time (PT), activated partial thromboplastin time (APTT) and fibrinogen were measured at various intervals throughout the studies. Plasma was collected from whole blood by centrifugation at 3250 RPM for 15 minutes. Erythrocyte sedimentation rate (ESR) and differential blood count pre- and post-pulsing were evaluated to determine potential alterations associated with electroporation.

ESR of the post-pulse samples were obtained over a four hour interval and tested by the Westergren method. These values remained in the normal range (0 to 20 mm/hr).

Routine clotting assays performed included pre- and post-pulsing measurement of PT, fibrinogen and APTT at various time intervals throughout the experiment, and were normal as well. The PT ranged from 6.2 to 8.0 seconds before pulsing to 6.4 to 9.3 seconds after pulsing. The APTT changed from 14.0 to 19.0 seconds pre- and post-pulse states, ranging from 177 to 202 mg/dL.

Post-pulsing blood cell count were within the normal physiological range. Blood films stained with Wright or Giemsa procedures showed no cellular deformation.

Light Microspcopy of Arterial Tissue

Electropulsing had no effect upon tissue morphology. Damage caused by balloon injury to the endothelial layer and, less frequently, to the internal elastic lamina was observed in the paraffin-embedded tissue sections stained with hematoxylin-eosin and observed under a light microscope at low and high power magnification.

EXAMPLE II

This example shows that an electrical impulse applied to a vessel of an animal increases the vessel luminal area.

Luminal area measurements of the arterial tissue sections were made by NIH image analysis software. Measurement of areas enclosed by the lumen in pulsed artery samples and non-pulsed (control) samples were performed in multiple sections in a given experiment. Statistical testing was performed with "instat" software (Graphpad, San Diego, Calif.). Results were considered statistically significant when the probability of error was $p\_0.05$.

A total of 120 serial tissue sections obtained from eight animals were examined. Fifty-seven sections were from electrically pulsed arteries and sixty-three sections were from non-electrically pulsed arteries. All experiments but one showed expansion of the vessel lumen after electropulsing at approximately 65 volts and a pulse length of 9 ms. The luminal vessel layer of the pulsed artery showed an average increase of 76% in area over the non-pulsed. The Wilcoxon signed rank test for paired non-parametric data showed a significant increase ($2p\_0.0156$) in lumenal vessel area of the electropulsed artery. The effect of applying an electrical impulse via electroporation on the luminal area of an artery, as observed histologically and graphically are shown in FIGS. 5 and 6, respectively.

The observed expansion of the vessel lumen does not appear to be due to artifacts resulting from the histological preparation of the arteries because Kakuta et al. (*Circulation* 89:2809–2815 (1994)) has reported a linear correlation of the lumen area obtained by histology and angiography and the atherosclerotic rabbit model.

Expansion of the arterial luminal area as a result of electropulsing can provide an avenue to achieve maximum dilatation during PTCA. The expansion of vessel lumen observed in pulsed arteries may be due to the activation of endothelium derived relaxation factors (EDRF), now believed to be the same as nitric oxide (NO), or the release of other vasodilating substances triggered by electrical pulses. If this vasodilation mechanism involves a nitrous oxide medicated event, it would probably entail inhibition of platelet aggregation, cell adhesion and also vasospasm, which can occur during PTCA.

EXAMPLE III

This example shows that the application of an electrical impulse to a vessel of an animal can deliver a composition into the vessel.

Fluoresceinated heparin (F-heparin; 167 units/mg of activity) was used as a probe. To ensure that the covalent bonded fluorescein had not been dissociated by electroporation, in vitro experiments were performed in an electroporation cuvette containing F-heparin. The solution was pulsed using the same electrical parameters as used in the in vivo studies. The sample was then loaded in a LKB ultropak column (TSK G4000 sw) connected to an Anspec HPLC pump with a Shimadzu (SPD-6AV) UV-VIS spectrophotometric detector for analysis. The hard copy of the HPLC profile was obtained using Hitachi D-2500 chromato-integrator. Individual samples were also analyzed in a luminescence spectrometer (Perkin-Elmer LB-5, CA) at 490 nm excitation and emission at 520 nm.

Luminescence spectrometry and HPLC of electroporated F-heparin showed no differences from the non-electroporated sample. We also obtained an HPLC analysis of FITC in the non-electroporated condition. Analysis of F-heparin electroplated in vitro at voltages and pulse lengths used in in vivo rabbit experiments did not show presence of free FITC. Thus, pulsing does not appear to change the structure of F-heparin, and therefore, the fluorescence observed in control and treated tissue samples is predominantly that of FITC-conjugated heparin.

F-heparin penetration into the arterial wall was tested by both direct and indirect visualization. For direct visualization of heparin fluorescence, tissues were excited at 488 nm and emission observed at 520 nm in a fluorescent microscope with fluorescent isothiocyanate (FITC) filter. Pseudocolor images coding for fluorescence emission were obtained from a linear look-up table ('LUT') using NIH image analysis software. Photographs were obtained by dye-sublimation photocopy with a Tektronix phaser 440-color printer.

For indirect visualization, tissue sections were hydrated in Tris-buffered saline (TBS, pH 7.6) and treated with 3% $H_2O_2$ for 30 minutes to inhibit an endogenous peroxidase activity. After incubation with 10% normal goat serum to block non-specific binding sites, the monoclonal antibody to FITC (1:250, clone FL-D6; Sigma, Mo.) was applied for 16 hours at 4° C. After rinsing with 1% normal goat serum in TBS and incubation for 10 minutes in 10% of the same serum, goat antisera to mouse IgG (1:50) was applied for 30 minutes, followed by incubation with the mouse peroxidase complex (1:250; Stemberger monoclonals). Sections were developed using 3, 3, M-^S-diaminobenzidine in 0.3% $H_2O_2$, 50 mM Tris-HCl (pH 7.6) for identical periods, so direct comparison could be made.

As shown in FIG. 7B, pseudocolor image manipulation by NIH image analysis software of the fluorescence emission by FITC-conjugated heparin showed intense fluorescence of the pulsed artery in both the tunica media and tunica adventitia of the arterial cross section. Heparin was found to be inhomogeneously distributed around the arterial circumference, which could be due to non-uniformity of the electrical field strength in different parts of the artery caused by variations in local tissue resistance. It is clear, however, that pulsing increases heparin penetration to the deeper part of the tissue several folds with respect to the control.

A qualitative measurement of heparin in the tissue with monoclonal antibody to FITC, followed by peroxidase staining, also shows that pulsing facilitates heparin binding in the tissue (FIG. 8). At very high magnification of the image, one could clearly see the presence of the antibody in the cytosol.

These data show the feasibility of using an electroporation catheter for the endovascular delivery of molecules, such as heparin. The observation of increased F-heparin fluorescence by direct visualization under a fluorescence microscope and increased binding of antibody to fluorescein by indirect visualization in electroporated arteries confirms the ability of electroporation to facilitate entry and retention of heparin into the arterial wall. Thus, this data show that endovascular electropulsing may provide better delivery, retention and greater therapeutic efficacy than that achieved by conventional delivery of heparin. Electropulsing is therefore applicable for clinical situations in which catheters have traditionally been used, including those other than endovascular diseases.

In earlier studies we demonstrated the penetration of a marker gene (lacZ driven by a CMV promoter) into the arterial wall by pulsing with caliper electrodes placed across the extraluminal adventitial surface. The punctate location of gene expression inside the arterial wall of rabbit carotid arteries remained for three weeks (Giordano et al., Abstract #780-4, Amer. Coll. Cardiol. Meeting, Orlando, Fla., March 1996).

Subsequently, antisense RNA directed towards PCNA and CDC-2 kinase sequences has been successfully delivered in porcine arteries using an electroporation catheter. Pulsed arteries showed higher uptake of the antisense oligonucleotide compared to the control. These results show that delivery of heparin by electroporation is possible (Wolinsky et al., *J. Am. Coll. Cardiol.* 15:475–481 (1990); Gimple et al., *Circulation* 86:1536–1546 (1992); Femandez-Ortiz et al., *Circulation* 89:1518–1522 (1994)) and suggest the usefulness of electrical pulse-assisted local delivery of other molecules. For example, pulse-assisted delivery can be useful for the local or systemic delivery of other molecules which are of low effectiveness when delivered conventionally (Fareed et al., *Sem. Thromb. Hemos.* 17:455–470 (1991)).

The data show that vasodilation of a vessel can be induced by applying an electrical impulse. The data also show that the flow of fluid through a vessel can be increased by applying an electrical impulse. Based on the pulse-enhanced induction of vessel vasodilation and the increase of flow of fluid through the vessel, it is contemplated that the methods of the invention when applied to clinical situations, would avoid complications due to the side effects associated with various drugs. Additionally, the data show that compositions, such as heparin, can be effectively delivered into vessel tissue using the methods of the invention. This also would avoid clinical complications that arise due to excess drug in the systemic circulation. The methods additionally allow the delivery of compositions into different depths of the artery simply by changing the electrical parameters. Endovascular electroporation can therefore provide better retention and higher therapeutic efficacy than that achieved by conventional systemic delivery of heparin at clinically safe concentrations.

What is claimed is:

1. A method far increasing flow of a fluid medium through a vessel in a subject comprising the steps of:

(a) contracting the interior membrane of said vessel with a plurality of electrodes;

(b) applying to at least a first electrode and a second electrode in said plurality of electrodes at least one electrical impulse of a sufficient voltage to cause the muscles surrounding the tissue comprising a lumen of the vessel to temporarily relax to allow the vessel to dilate and thereby increase the flow of a fluid medium through the vessel, wherein said vessel is selected from the group consisting of a blood vessel and a lymphatic vessel; and (c) determining that the flow of a fluid medium through said vessel has been increased.

2. The method according to claim 1, wherein said voltage is between about 50 volts and about 90 volts.

3. The method according to claim 1, wherein application of said electrical impulse ranges from about 0.5 milliseconds to about 15 milliseconds.

4. The method according to claim 3, wherein the at least one electrical impulse is multiple electrical impulses.

5. The method according to claim 1, wherein said vessel is a blood vessel selected from the group consisting of an artery, a vein, and a capillary.

6. The method according to claim 1, wherein said method is used to treat a vessel that is blocked or narrowed due to a condition selected from the group consisting of restenosis, a blood clot, and constriction or blockage resulting from an external force.

7. The method according to claim 1, wherein step (a) is performed with a catheter comprising said electrodes.

8. The method according to claim 7, wherein said catheter further comprises at least one inflatable balloon and step (a) further comprises inflating said balloon during application of said electrical impulse.

9. The method according to claim 1, further comprising denuding an endothelial lining of said vessel prior to, simultaneously with, or after applying said electrical impulse.

10. The method according to claim 1, wherein application of said at least one electrical impulse occurs without the presence of an exogenous therapeutic composition.

11. The method according to claim 1, wherein the vessel is a lymphatic vessel that is a lymphatic duct.

12. The method according to claim 1, wherein the vessel is an artery selected from the group consisting of a carotid artery, a coronary artery, an iliac artery, and the aorta.

* * * * *